United States Patent [19]

Schnipelsky et al.

[11] Patent Number: 5,229,297
[45] Date of Patent: Jul. 20, 1993

[54] CONTAINMENT CUVETTE FOR PCR AND METHOD OF USE

[75] Inventors: Paul N. Schnipelsky, Rochester; Leonard J. Seaberg, Penfield; Charles C. Hinckley, Pittsford; Jeffrey A. Wellman, Rochester; William H. Donish, Rochester; John B. Findlay, Rochester, all of N.Y.

[73] Assignee: Eastman Kodak Company, Rochester, N.Y.

[21] Appl. No.: 962,159

[22] Filed: Oct. 15, 1992

Related U.S. Application Data

[63] Continuation of Ser. No. 673,053, Mar. 21, 1991, abandoned, which is a continuation-in-part of Ser. No. 339,923, Apr. 17, 1989, abandoned, which is a continuation-in-part of Ser. No. 306,735, Feb. 3, 1989, abandoned.

[51] Int. Cl.$^5$ ............... C12Q 1/68; G01N 33/00
[52] U.S. Cl. ............... 436/94; 435/6;
435/91; 435/172.3; 435/301; 436/63; 436/501;
436/508; 436/180; 935/77; 935/78
[58] Field of Search ............ 435/6, 91, 172.3, 301;
436/63, 86, 94, 180, 501, 508, 808, 809, 815;
935/77, 78

[56] References Cited

U.S. PATENT DOCUMENTS

| | | | |
|---|---|---|---|
| 3,036,894 | 5/1962 | Forestiere | 23/230 |
| 3,647,386 | 3/1972 | Gilford | 23/230 |
| 3,690,836 | 9/1972 | Buissiere et al. | 23/253 |
| 3,691,017 | 9/1972 | Brown et al. | 195/103.5 |
| 3,713,779 | 1/1973 | Sirago et al. | 23/259 |
| 3,726,645 | 4/1973 | Kaczmarek | 23/253 |
| 3,740,196 | 6/1973 | Stroterhoff | 23/253 |
| 3,799,742 | 3/1974 | Coleman | 23/253 |
| 3,994,594 | 11/1976 | Sandrock et al. | 356/246 |
| 4,007,010 | 2/1977 | Woodbridge, III | 23/253 R |
| 4,065,263 | 12/1977 | Woodbridge, III | 23/253 |
| 4,119,407 | 10/1978 | Goldstein et al. | 422/58 |
| 4,585,623 | 4/1986 | Chandler | 422/57 |
| 4,673,657 | 6/1987 | Christian | 436/501 |
| 4,683,195 | 7/1987 | Mullis et al. | 436/6 |
| 4,690,801 | 9/1987 | Anderson | 422/68 |
| 4,756,884 | 7/1988 | Hillman et al. | 422/73 |
| 4,806,313 | 2/1989 | Ebersole et al. | 422/61 |
| 4,810,653 | 3/1989 | Helfer et al. | 435/316 |
| 4,902,624 | 2/1990 | Columbus et al. | 435/316 |
| 5,154,888 | 10/1992 | Zander et al. | 422/58 |

FOREIGN PATENT DOCUMENTS

| | | |
|---|---|---|
| 0281201 | 3/1988 | European Pat. Off. |
| 0320240 | 6/1989 | European Pat. Off. |
| 2612295 | 9/1988 | France |
| 86/00704 | 1/1986 | World Int. Prop. O. |

*Primary Examiner*—James C. Housel
*Assistant Examiner*—Long V. Le
*Attorney, Agent, or Firm*—Dana M. Schmidt

[57] ABSTRACT

A cuvette and a method of use which prevent nucleic acid amplified by PCR technology from being released to the atmosphere, while still proceeding to a detection step to determine whether or not the nucleic acid is present. Detection reagents are either pre-incorporated into compartments in the cuvette or added after amplification. In the latter case, a check valve prevents amplified nucleic acid from being released. Transfer of liquids between compartments is achieved via the use of flexible compartment walls and an external pressure source, or via pistons that are part of the cuvette and operate on the compartments as a piston within a piston chamber.

15 Claims, 9 Drawing Sheets

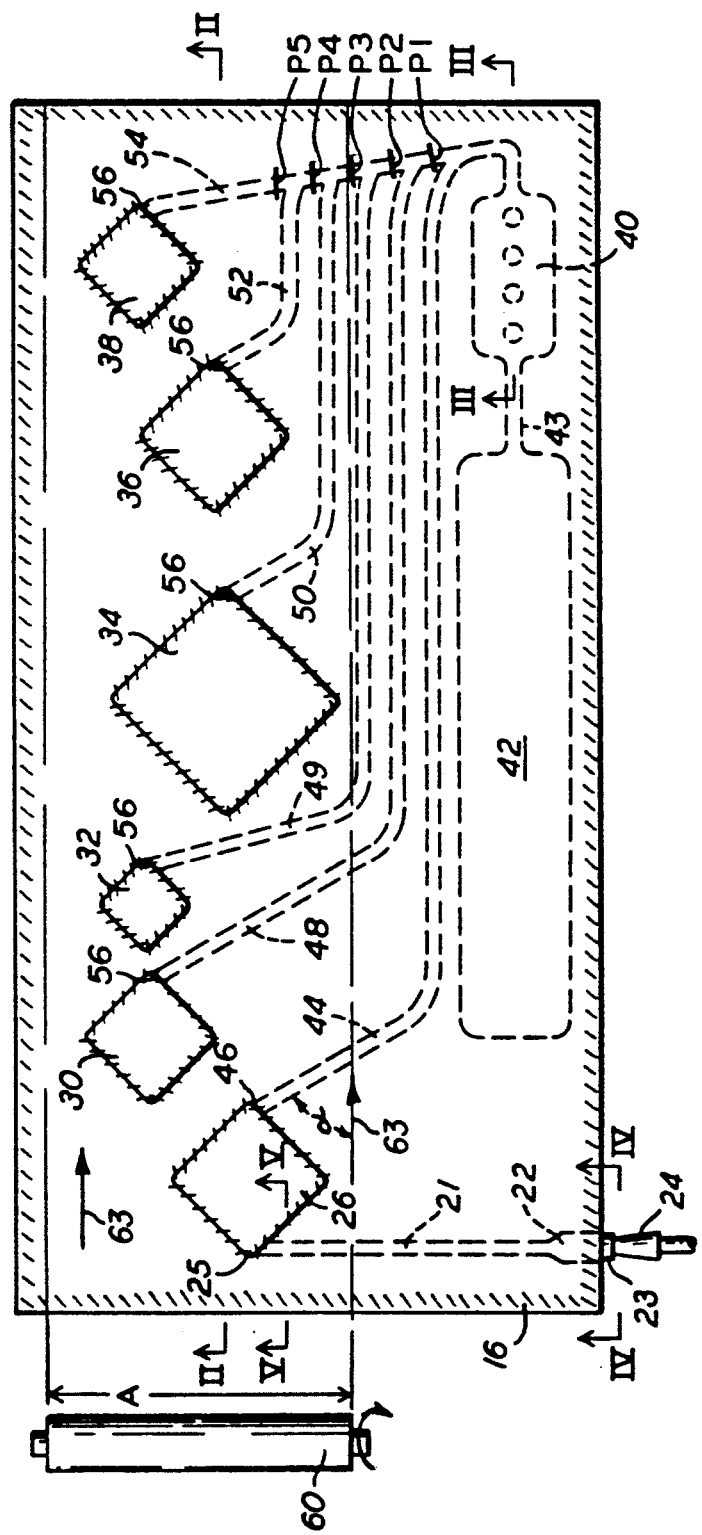
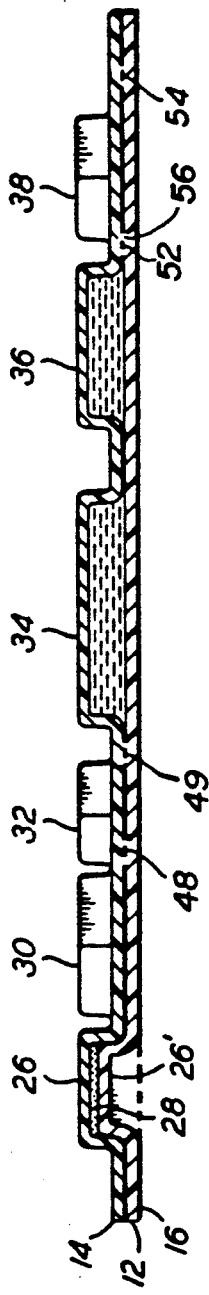
FIG. 1
FIG. 2

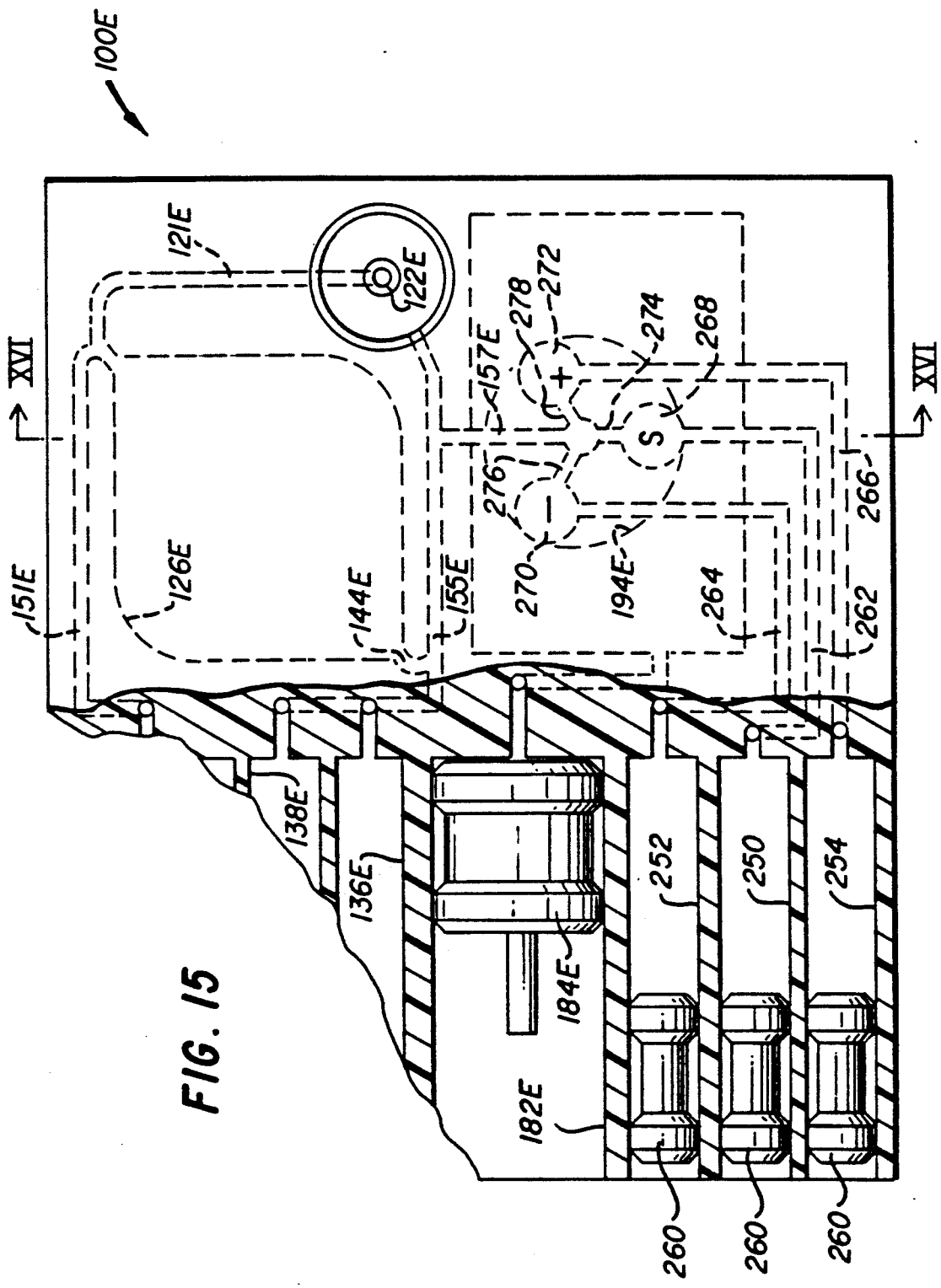

CONTAINMENT CUVETTE FOR PCR AND METHOD OF USE

RELATED APPLICATIONS

This ia a continuation of application Ser. No. 673,053, filed Mar. 21, 1991, now abandoned, which is a Continuation-in-Part application of U.S. Ser. No. 339,923 filed on Apr. 17, 1989, now abandoned, which is a Continuation-in-Part application of U.S. Ser. No. 306,735 filed on Feb. 3, 1989, now abandoned.

FIELD OF THE INVENTION

This invention relates to cuvettes in which reactions are undertaken to amplify and detect nucleic acids, using PCR technology, without exposing the environment to amplified nucleic acid.

BACKGROUND OF THE INVENTION

Polymerase chain reaction (PCR) technology is only one of several techniques that permit nucleic acid material, such as DNA, often extracted from as little as a single cell, to be amplified to hundreds of millions of copies. This is important since prior to PCR technology it was virtually impossible to detect a single DNA strand. However, when a single DNA strand, such as the DNA of the human immunodeficiency virus (HIV, otherwise known to cause AIDS), is added to amplifying reagents that will amplify the DNA of choice, hundreds of millions of copies of that DNA can be obtained in a relatively short time. Technology further allows for the detection of the amplified nucleic acid material (DNA for example), using probes that hybridize to the amplified material of choice, such probes in turn either being immobilized or immobilizable to a solid support, such as a filter membrane, and/or being labeled for detection using enzymes or other moieties.

Conventionally, this has been done by amplifying the nucleic acid material in a stoppered plastic container until the desired number of copies have been formed. Thereafter, the container is reopened, such as by unstoppering, and either the amplified copies are withdrawn and transferred to detection apparatus, or detecting reagents can be added to the container used for the amplification, so that detection is done in the same container.

It has been discovered that such a technique is unsatisfactory for convenient and widespread use of, e.g., PCR technology, because aerosols are produced in the act of unstoppering and/or transfer of fluids. Such aerosols contain a few of the amplified nucleic acid material, e.g., DNA. The aerosols then proceed to disperse within the environment. Normally, such few molecules in the environment are not of great concern. *However*, only one DNA molecule is needed to ruin by contamination *other* amplifying containers yet to be used for detection. That is, if the errant DNA molecule floats into or is carried, inadvertently, by an operator to another amplifying container yet to be used, that one molecule is all that is needed to provide the DNA needed for the next amplification. Needless to say, if the point of the next test is to see if a particular DNA is present (e.g., for HIV), and it is detected only because of the errant DNA and not that of the patient, the test is ruined. Thus, the very power of DNA amplification becomes the source of potential ruin of the tests. As a matter of fact, an entire lab has been proven to be contaminated by the unstoppering of just a few containers in which the sample has already been amplified. Although such a problem might be avoidable by using highly skilled and trained personnel who painstakingly minimize the aerosols produced, the need for such labor makes the technology impractical for general use.

Thus, it has been a problem prior to this invention to provide apparatus and a method for amplifying and detecting nucleic acid material, without contaminating the surrounding environment.

Yet another problem has been, prior to this invention, to automate the detection steps, that is, minimize the need for operator intervention. The need to transfer amplified nucleic acid material or to add detection reagents makes such automation difficult.

SUMMARY OF THE INVENTION

The above problems are addressed by an apparatus and a method that solve the above-mentioned needs. The invention is based upon the realization that the contamination can be prevented by confining the amplifying reagents *and* amplified nucleic acid in the cuvette so that it is impossible for any amplified nucleic acid molecules to escape.

More specifically, in accord with one aspect of the invention, there is provided a cuvette for the amplification and detection of DNA, the cuvette including a plurality of compartments including a) means for allowing DNA amplification, the allowing means including a reaction compartment and means adjacent to the reaction compartment for permitting active or passive cycling of the contents of the reaction compartment through a temperature range of from about 30° C. to about 95° C.; b) means for providing liquid interconnection between the compartments by pressurizing the liquid; and c) means for trapping and holding DNA at a detection site for detection, including a detection material capable of generating a detectable signal. The cuvette is improved in that some of the compartments contain the detection material and the reagent in unreacted form in storage, while the cuvette is free of DNA sample, whereby the cuvette need not be reopened between DNA amplification and detection.

In accord with another aspect of the invention, there is provided a closed, disposable cuvette for carrying out amplification and detection of nucleic acid material, comprising: a plurality of compartments including a reaction compartment, means permitting active or passive cycling of the contents of the reaction compartment through a temperature range; at least one detection material being present in at least one of the compartments; and means for fluidly interconnecting the compartments in prescribed order when pressure is applied to the contents of a compartment. The cuvette is improved in that the compartments all are closed to fluid flow to locations outside of the container and said reaction compartment contains nucleic acid material and unreacted amplifying reagents; at least one of the compartments including means at a detection site therein for immobilizing the nucleic acid material for detection after amplification, so that detection of amplified nucleic acid material occurs without contamination of other containers or apparatus by the amplified nucleic acid material. The result is that detection of amplified nucleic acid material occurs without contamination of other containers or apparatus by the amplified nucleic acid material.

In accordance with still another aspect of the invention, there is provided a closed cuvette as described in the previous paragraph, wherein the reagent contents of the reaction compartment comprise polymerase enzyme, primer nucleic acids and deoxyribonucleotides.

In accord with yet another aspect of the invention, there is provided an apparatus for amplifying and detecting DNA, comprising a cuvette containing i) a plurality of compartments and means for interconnecting each of them to at least one other compartment, the compartments including a) at least one reaction compartment for amplifying DNA strands, b) at least one detection compartment for detecting amplified DNA and including a detection site, and c) means for delivering a detection material to amplified DNA strands; ii) means for permitting active or passive cycling of the contents of the reaction compartment through a temperature range; and iii) liquid access means connected only to the at least one reaction compartment for allowing the injection into the reaction compartment of a sample DNA for amplifying; characterized in that the cuvette further includes iv) means sealing the cuvette against passage of DNA after sample DNA is injected; and the apparatus further includes means for moving at least the detection material and a DNA strand into the detection compartment and onto the detection site; so that once a DNA sample is injected into the compartments and the access aperture is closed, the fluid contents of the compartments are contained against contact by the operator and environment during the entire amplification and detection reaction.

In still another aspect of the invention, there is provided a method for amplifying and detecting nucleic acid material in a closed cuvette without allowing aerosols to exit therefrom to contaminate the environment, the method comprising the steps of a) injecting a sample of nucleic acid material into a cuvette comprising a plurality of compartments including a reaction compartment wherein amplifying reagents are present, and a storage compartment for use with a detection material, at least one of the compartments including a detection site, and means for interconnecting the compartments to provide fluid transfer; b) closing off permanently the portions of the cuvette containing the nucleic acid material to lock all nucleic acid into the cuvette; c) amplifying the nucleic acid material by cycling the cuvette through temperature changes preselected to cause the reagents to be effective; d) fluidly transferring amplified nucleic acid material from the reaction chamber to the detection site; e) fluidly transferring detection material to the detection site while keeping the cuvette closed; and f) detecting the amplified nucleic acid material at the detection site with the detection material, all while the nucleic acid material remains confined within the cuvette.

It is an advantageous feature of the invention that a cuvette is provided for amplifying nucleic acids that avoids the risk of contaminating the environment with amplified nucleic acid since it avoids reopening the area of the cuvette containing such nucleic acid.

It is a related advantageous feature of the invention that a cuvette is provided that can be used for such amplification by relatively unskilled labor.

It is another advantageous feature of the invention that such a cuvette is provided that is amenable to automated processing.

Other advantageous features will become apparent upon reference to the detailed description that follows, and the attached drawings.

BRIEF DESCRIPTION OF THE DRAWINGS

FIG. 1 is a plan view of a cuvette constructed in accordance with the invention;

FIG. 2 is a section view taken generally along the line II—II of FIG. 1;

FIGS. 14 and 15 are fragmentary plan views partially in section, similar to FIG. 9 but illustrating alternate embodiments;

DESCRIPTION OF THE PREFERRED EMBODIMENTS

Figure 3:
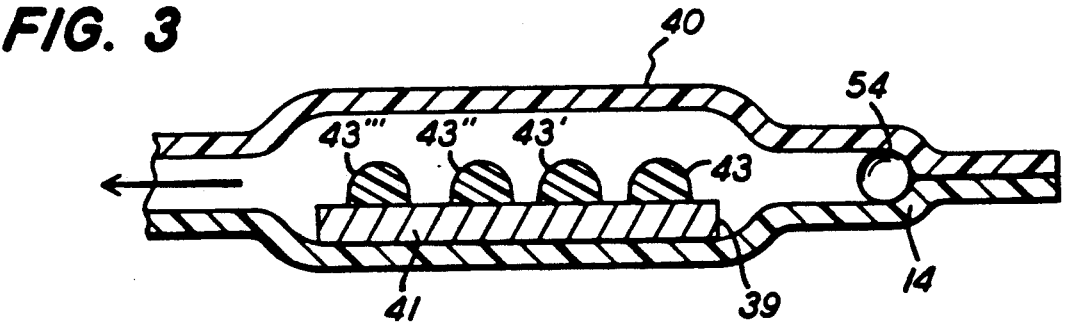
FIG. 3 is a section view taken generally along the line of III—III of FIG. 1.

The invention is hereinafter described primarily with respect to the use of PCR technology to amplify and detect DNA, using particular preferred cuvette configurations. In addition, it is useful with any method of nucleic acid amplification, to amplify nucleic acid from any source, in any cuvette, so long as the apparatus and method prevent amplified nucleic acid from exiting the cuvette in any form. The nucleic acid can be obtained, for example, from plasmids or cloned DNA or RNA, or from natural DNA or RNA from any source, including bacteria, yeast, viruses, cells infected by viruses or bacteria, plants or animals. DNA or RNA may be extracted from blood or tissue materials. Another method of amplification called transcription-based amplification and which is different from PCR, that can benefit from the containment cuvette of this invention, is described in *Proc. Natl. Acad. Sci. USA*, Volume 86, page 1173-1177, February, 1989 (Biochemistry).

PCR TECHNOLOGY

Nucleic acid amplification generally proceeds via a particular protocol. One useful protocol is that set forth in U.S. Pat. No. 4,683,195. Briefly, that protocol features, in the case of DNA amplification, the steps of:

1) Obtaining a sample suspected of containing at least one specific nucleic acid sequence of interest;

2) Denaturing the sample to separate the strands;

3) Contacting the sample with primers, an extension enzyme such as polymerase and other amplification components useful to replicate the nucleic acid;

4) Repeating steps #2 and #3 as many times as necessary; and

5) Detecting the amplified DNA.

A preferred protocol within this class is as follows:

1) A complete DNA double helix is optionally chemically excised, using an appropriate restriction enzyme(s), to isolate the region of interest.

2) A solution of the isolated nucleic acid portion (here, DNA) and nucleotides is heated to and maintained at 92°-95° C. for a length of time, e.g., no more than about 10 minutes, to denature the two nucleic acid strands; i.e., cause them to unwind and separate and form a template.

3) The solution is then cooled through a 30° C.-60° C. zone, to cause a primer to anneal or "attach" to each of the two template strands. To make sure this happens, the solution is held at an appropriate temperature, such as about 55° C. for about 15 seconds, in an "incubation" zone.

4) The solution is then heated to and held at about 70° C., to cause an extension enzyme, preferably a thermostable polymerase enzyme, to extend the primers bound to the template strands by using the deoxyribonucleotides that are present.

5) The completed new pair of strands is heated to 92°-95° C. again, for about 10-15 seconds, to cause this pair to separate.

6) Steps 3)-5) are then repeated a number of times until the appropriate number of strands are obtained. The more repetitions, the greater the number of multiples of the nucleic acid (here, DNA) that is produced. Preferably the desired concentration of nucleic acid is reached in a minimum amount of time, wherein each cycle takes less than one minute. However, as much as five minutes can be used for one cycle.

As used herein, the term "primer" refers to an oligonucleotide, whether naturally occurring or synthetically produced, which is capable of acting as a point of initiation of synthesis when placed under conditions in which synthesis of a primer extension product complementary to a nucleic acid strand is induced. Such conditions include the presence of nucleotides (such as the four standard deoxyribonucleotide triphosphates) and an agent for polymerization such as a DNA polymerase, and suitable temperature and pH. Generally, each primer used in this invention will have from 15 to 40 nucleotides, and preferably, it has from 20 to 25 nucleotides.

All of this is preferably done in a cuvette, using a cycling of temperature between about 30° C. and about 95° C. The cuvette of the present invention provides a practical approach to allowing PCR technology to be practiced routinely by technicians and those of lesser skills, in an accurate fashion. For a complete understanding of the invention, further details of the PCR technology as it is practiced with this invention will be enumerated first.

Any DNA can be selectively replicated hundreds of millions of times. Selection of the appropriate primer nucleic acid strands insures that, under the best conditions, primarily the DNA of choice will replicate. Preferably, all primers are biotinylated when incorporated into the cuvette, to allow detection to proceed as described hereinafter. Heating of the target DNA now attached to a primer, in the presence of an extension enzyme, produces a double strand that includes a copy of the DNA of choice. The new pair so formed is then separated by very short periods of high temperature denaturing, and the process repeated. This is all done in one reaction compartment by insuring that the primers, deoxyribonucleotides and extension enzymes are present when the sample is added, either as pre-incorporated reagents or reagents that are added with the DNA. If pre-incorporated, the reagents can be applied by spraying and drying, and can include a polymerase, salts, buffers, stabilizers, and the nucleotides needed for replication.

The polymerase enzyme is useful regardless of its source. Preferably, it is the polymerase naturally produced from *Thermus aquaticus,* hereinafter "TAQ", or any synthetic equivalent such as that which is genetically engineered, as described, for example, in EPO publication 258,017.

The presence of the enzymes emphasizes the need for rapid thermal cycling, and short residence times at high temperatures. The 92°-95° C. denaturing temperature is close to the deactivation temperature of the enzymes, thus rendering unsatisfactory long heating periods.

Thereafter, the replicated DNA is identified, preferably by moving it to a detection compartment, to which suitable detection material is added or contained therein. In the prior art methods, such "movement" of the replicated DNA, and/or the addition of the reagents such as detection probes, has necessitated the reopening of the reaction compartment containing the DNA, creating the aerosol problem noted above. The detection involves the use of conventional materials capable of bonding via a complementary sequence of nucleotides to a replicated DNA strand. Such materials also include appropriate means that can be used to trap and hold the DNA at a detection site, such as in a detection compartment. Preferably, such appropriate means feature a membrane and/or a bead that is trapped.

Detection requires generally an immobilizing material and a signal generating material. Preferably, a primer used to replicate the DNA is already biotinylated, so as to react with avidin that is attached to either the immobilizing material or the signal-generating material. If the avidin is attached to the immobilizing material (such as a bead), hereinafter, the "avidin-bead capture" method, then a detection probe is used with a nucleotide sequence that hybridizes with replicated primer and which either itself generates a signal (for example, by being radioactive), or reacts with a reagent that produces a signal. For example, the detection probe can be attached to any appropriate signal-generating moiety, preferably enzymes, for example, horseradish peroxidase, capable of reacting with a leuco dye to produce a detectable signal (e.g., a color change.) The technology for attaching a signal generating moiety or an immobilizing material to a probe at the 3' or 5' end is known. For example in "Efficient Methods for Attachment of Thiol Specific Probes to the 3' End of Synthetic Oligodeoxyribonucleotides", Vol. 15 of *Nucleic Acids Research,* p. 5303 (1987), the techniques useful for the 3' end attachment are discussed. The articles discussing 5' end attachment are legion, for which the following is only representative: "Introduction of 5'

Terminal Functional Groups. . . .", Vol. 164 of *Analytical Biochemistry*, p. 336 (1987). It will be readily apparent that either the 3' or the 5' end can be used to attach the signal-generating moiety on the immobilizing material.

Thus, as used herein the term "probe" refers to an oligonucleotide, naturally occurring or synthetically produced, which does not act like a primer, but which is designed to be substantially complementary to one or more sequences of a nucleic acid so as to form a hybridized product. Further, a probe is generally designed for either "capture" or "detection" of the resulting hybridized product.

Alternatively, the detection probe and the immobilizing probe can be one and the same, attached at say, just the 5' end, using the techniques taught in the aforesaid *Analytical Biochemistry* article.

As noted above, the avidin can be attached to the signal-generating material, such as horseradish peroxidase, hereinafter the "oligo capture" method. In such a case, the immobilizing of the DNA is preferably achieved by an immobilizing probe, which is a nucleotide sequence that hybridizes with the replicated biotinylated primer, such sequence being attached to a polymer bead.

Thus, as used herein, "detection material" includes a probe on the replicated, biotinylated primer, that either itself generates a detectable signal or reacts with a reagent to produce a detectable signal. In the latter case, the detection material also includes such reagent.

The cuvette containing all detection materials, as well as the amplified DNA, can be agitated or shaken to promote mixing, and annealing of probes to the targeted DNA is achieved by conventional temperature cycling.

The hybridizing of the probes to the DNA can be done prior to or after transfer, if any, to the detection site.

Thereafter, all liquid is drawn off from the detection site. At this point, some of the detection material either is part of a replicated DNA strand or is hybridized to the DNA strand, and the DNA is captured by the surface of the membrane. Any DNA strand lacking the means for immobilizing it passes beyond the membrane.

The final step is to inject into the detection compartment a liquid containing a leuco dye or some other dye precursor capable of reacting with the detection material projecting from the DNA strands captured on the membrane. Useful leuco dyes include those set forth in U.S. Pat. No. 4,089,747, preferably in combination with a solubilizing polymer such as poly(vinyl pyrrolidone). A preferred example of the dye is 2-(4-hydroxy-3,5-dimethoxyphenyl)-4,5-bis(4-methoxyphenyl)imidazole, since this gives about 1000 dye molecules per 1 molecule of horseradish peroxidase.

As noted, the DNA can attach to or be hybridized to a probe on a bead. The beads are selected to be trapped by the detection membrane. Useful material for such beads includes any polymer that has useful reactive groups for bonding to either avidin or to a probe that will hybridize to the DNA. Conventional covalent attachments of avidin via active halogen atoms, 2-substituted activated ethylsulfonyl, or vinylsulfonyl groups on such polymers are known. Thus, copolymers of m and p-(2-chloroethylsulfonylmethyl)styrene are useful, for example, for such beads.

There are two key aspects of this invention that make the aforedescribed procedure practical. The first is to use an efficient thermal transfer so that the contents of the reaction compartment are quickly heated and then quickly cooled. Means permitting either active or passive heating and cooling are useful, providing active or passive cycling. That is, a Peltier device can be mounted in the reaction compartment to provide a heat transfer wall bordering the compartment. Preferably, however, the heat transfer is achieved by passive means, wherein the heat transfer material is a major wall surface of the reaction compartment. The heat source or heat sink is then supplied from an exterior source, most preferably on *both* sides of the cuvette.

The second key aspect is to construct the cuvette compartments to prevent amplified nucleic acid from escaping. That is, the compartments must be sealed against leakage to the environment, once amplification occurs. A preferred construction is one in which the compartments have pre-incorporated all reagents before DNA is introduced, and locking means are used to lock the cuvette against leakage after DNA introduction. In such embodiments, means are provided for bringing about liquid communication between compartments within the closed cuvette, preferably using applied pressure, to obtain the necessary reactions.

THERMAL CYCLING

Considering first the preferred thermal transfer mechanism, namely the passive transfer wall of the compartment, the material of such wall is selected to provide a predetermined thermal path length and thermal resistance that will provide a high rate of thermal energy transfer. Most preferably, such path length is no greater than about 0.3 mm, and the thermal resistance for a cross-sectional area of one $cm^2$ is no greater than about 5.0° C./watt. These properties are readily achieved by constructing the thermal transfer wall out of a plastic, or a laminate of plastic and metal such as aluminum that is about 0.05 mm thick. Such aluminum has a thermal resistance R, calculated as thickness x/(conductivity K times surface area A), which is about 0.003° C./watt. (These values can be contrasted for ordinary glass of the same thickness, which has a thermal resistance of about 0.24° C./watt.) The plastic, which is preferably a heat-sealable coated polyester such as poly(ethylene terephthalate) coated on one or both sides with medium density polyethylene, has a thermal resistance of 1.06° C./watt for a preferred thickness of about 0.005 cm.

The thermal transfer wall can be secured to the other cuvette walls by any suitable means. One such means is a layer of a priming adhesive, which comprises for example a conventional high temperature acrylic adhesive, followed by a layer of conventional polyester adhesive. These adhesive layers can extend over the surface area of the thermal transfer wall, as such extensions can prevent the aluminum, if used, from interfering with reactions occurring within the cuvette. Alternatively, a plastic layer can cover the aluminum.

A cuvette constructed with such a thermal transfer wall has been found to produce a thermal time constant tau (t) for a volume of liquid of about 200 ml, that is no greater than about 10 seconds. Most preferred are those in which t is of the order of 3–8 seconds. That is, when such a cuvette, filled with water, is heated along the exterior of the thermal transfer wall, and its temperature is measured at point inside the reaction compartment on the other side of that wall, a thermal response curve can be generated from 28° C. to a final temperature of 103.9° C. The time it takes for the liquid therein to reach a temperature of 76° C. (63% of the difference (103.9−28)) is the value of tau (t). This derives (approximately) from the well-known thermal response equation:

Temperature T (t) = Final Temperature + (Initial Temperature − Final Temperature)·$\tau^{-t/t}$   1)

Thus, if the time interval t in question equals tau, then $\tau^{-t/t} = \tau^{-1} \approx 0.37$. In such a case, T (t) (at t=tau) is the temperature which is equal to the sum of the initial temperature, plus 63% of (Final Temperature−Initial Temperature). From such values, tau for the liquid in the cuvette turns out to be about 3.5 seconds. For the preferred configurations, using an intervening layer between the aluminum and the liquid in the reaction compartment, tau, the thermal time constant, is still no greater than about 10 seconds when the liquid in the cuvette is water.

Alternatively, the heat source can be a defocused laser. The use of just a clear polyester layer as the thermal transfer wall is preferred in such a case, and a dye is incorporated into the reaction compartment, having an absorption wavelength appropriate to the laser.

CONTAINMENT

Turning now to another aspect of the invention, the amplified DNA must be locked within the cuvette. This means that reagents needed for amplifications, that is, the primer strands, deoxyribonucleotides and the extension enzymes, are either pre-incorporated into the cuvette prior to addition of the sample of nucleic acid material, or they are added with the sample. Most preferably, the detection material is pre-incorporated prior to addition of the sample, so that after sample addition and prior to amplification, the cuvette is locked shut against leakage, there being no further access required. Alternatively, however, the cuvette can be constructed to allow the detection material to be added to storage compartments post amplification, subject to these provisions: 1) the storage compartment(s) to which they are added must be separate from the reaction compartment used for amplification, and 2) there must be provided means such as one-way check valves that allow such storage compartments to feed reagent to the amplified nucleic acid, but not amplified nucleic acid to the storage compartments.

In accordance with a further aspect of this invention, the cuvette is provided with means for providing communication between the storage compartments and the detection compartment. In one embodiment, such communications means include means such as pressurizing members for moving the reagents from the storage compartment to the detection site, for example, a separate detection compartment. Alternatively, and most preferably, the pressurizing means are exterior to the cuvette, and the walls of the cuvette are flexible enough to transmit pressure from the exterior to the interior, thus pressurizing and moving the reagents within the cuvette. Any external pressure source can be used, e.g., a pressure roller or a piston from an air cylinder.

EXEMPLARY CUVETTE EMBODIMENTS

The cuvette 10 of the invention can feature flexible compartments, FIG. 1, that cooperate with an external pressurizing means 60, such as a pressure roller, to provide the total apparatus of the invention. More particularly, cuvette 10 comprises two relatively thin sheets 12, 14 formed such as by molding to mate together with pockets or compartments and connecting passageways protruding from the plane of the contacting sheets, FIG. 2. The sheets are secured together at least along their outer periphery 16, and preferably at all points surrounding compartments or passageways, such as by heat- and/or ultrasonic pressure-sealing. A heat-activatable adhesive such as ethylene vinyl acetate is useful for such joining operation. A liquid injection aperture 22 is the exception to the sealed periphery 16, for use with a mating pipette 24. Such aperture 22 optionally includes a rigid rim 23 extending into it, FIG. 4, within which a pipette 24 seats.

The compartments are as follows: compartment 26 is the reaction compartment, and optionally has the amplifying reagents 28 pre-incorporated therein, FIG. 2, in liquid or dried form. Compartment 30, FIG. 1, is a storage compartment for the first wash compartment containing wash water as a pre-incorporated reagent. Compartment 32 is a storage compartment containing at least one of the detection materials pre-incorporated therein, namely a biotinylated probe having at one end a complementary nucleotide for attachment to the amplified DNA, and preferably also a signal generating moiety, for example, avidin bound to the horseradish peroxidase discussed above. Storage compartment 34 is a second wash-containing storage compartment, which preferably has a much larger volume that the volume of storage compartment 32. Storage compartment 36 has pre-incorporated therein, the remaining detection reagents, namely a peroxide and a leuco dye, for example 2-(4-hydroxy-3,5-dimethoxyphenyl)-4,5-bis(4-methoxyphenyl)imidazole, preferably in combination with poly(viny pyrrolidone) as a stabilizer. Storage compartment 38 has pre-incorporated therein a stop solution to prevent too much leuco dye from converting to the dye, for example, a solution of sodium azide.

Finally, compartment 40 is the detection site for this embodiment, discussed hereinafter, and compartment 42 is the waste compartment, preferably initially deflated to provide for expansion as liquid is forced into it. Compartment 42 connects to compartment 40 via passageway 43. Optionally, a one-way check valve (not shown) can be included in passageway 44 to prevent waste liquid from backwashing into compartment 40, thus creating undesirable background color.

The interconnections are as follows: passageway 21 connects injection aperture 22 with compartment 26, passageway 44 connects reaction compartment 26 with detection compartment 40, except that a temporary seal is provided at 46 to keep introduced DNA in compartment 26 until pressure is generated by roller 60. Passageway 48 connects compartment 30, passageway 49 connects compartment 32, passageway 50 connects compartment 34, passageway 52 connects compartment 36 and passageway 54 connects compartment 38, all with detection compartment 40, again each preferably with a temporary seal 56, FIG. 2, interrupting flow out of the respective compartment until roller 60 breaks the seal. Passageway 54 serves as the trunk line to which the others (48, 49, 50 and 52) are joined.

The compartments are deliberately positioned, FIG. 1, so that each one will empty into compartment 40 in the proper sequence as roller 60 advances along path A in the direction of arrows 63. Thus, first the amplified DNA is pushed into compartment 40, then the first wash, then the detection probe from compartment 32, then the second wash, then the leuco dye solution and finally the stop solution. In some cases, the development of the dye from the leuco dye is done in the dark, for example, if the dye should fade readily in light. The respective passageways are also preferably constructed so as to be squeezed by the roller—that is, they are constructed to always form an angle to arrows 63 that is less than a right angle, within path A. (See, e.g., angle alpha, FIG. 1.) If they were to form a right angle, the roller would tend to jump over the passageway, rather than squeeze it.

It is not essential that *both* sheets 12 and 14 be collapsible by roller 60—only that at least one of them be, under a pressure of at least 170 g/cm. Pressures as high as 1500 g/cm are also useful. Thus, FIG. 5, sheet 12 can comprise a collapsible, relatively flexible plastic such as a heat-sealable polyester, for example, Scotchpak TM brand heat-sealable film no. 229 made by 3M, whereas sheet 14 can be less flexible and less collapsible, or it can be of the same flexibility as sheet 12.

Figure 5:
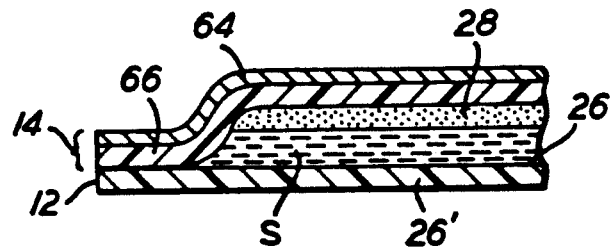
FIG. 5 is an enlarged, fragmentary section view taken along the line V—V of FIG. 1.

At least for compartment 26, sheet 14 can comprise a laminate of an aluminum foil 64 on the outside, FIG. 5, and a polymer layer 66 on the inside, preferably a layer of polyester, like sheet 12. The aluminum foil preferably has a thickness of between about 0.0013 cm and about 0.026 cm, and most preferably about 0.005 cm. Layer 66 has a thickness of between about 0.0013 and about 0.03, and most preferably about 0.005 cm. Even with layer 66 present, the thermal path length of compartment 26 is no more than about 0.3 mm and the thermal resistance does not exceed about 5.0° C./watt. The advantage of the laminate construction over a single sheet of plastic is that, once the compartment is crushed by the roller, the aluminum resists reinflation such as could allow backwashing to occur from liquids under pressure downstream. For this reason, sheet 14 is preferably so constructed as a laminate for the entire length of cuvette 10.

It is preferred that a liquid, when ejected from its compartment, not backwash up to the passageway used to empty another compartment that is further downstream. To this end, as roller 60 advances from left to right, FIG. 1, pinching means can be moved down onto cuvette 10 to pinch off the passageways as follows:

As roller 60 moves across compartment 26, pinching is done at point $P_1$. As it moves across compartment 30, pinching occurs at point $P_2$, and likewise at point $P_3$ for compartment 32, point $P_4$ for compartment 34 and point $P_5$ for compartment 36.

Figure 6:
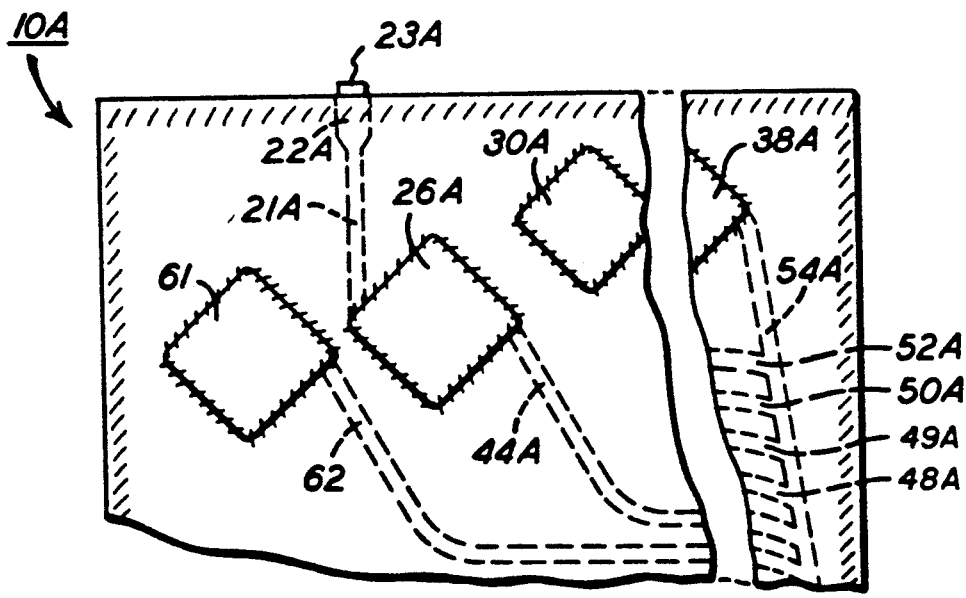
FIG. 6 is a fragmentary plan view similar to that of FIG. 1, but illustrating an alternate embodiment.

Alternatively, a prewash compartment can be included, FIG. 6, to insure that all the exit passageways are first filled with water, so that upstream compartments will not backwash into the passageways for downstream compartments. Parts similar to those previously described, bear the same reference numeral to which the distinguishing suffix "A" has been appended.

Thus, FIG. 6, the very first compartment to be encountered by roller 60 can be storage compartment 61 containing wash water that empties via passageway 62 to trunk line 54A. The rest of the passageways 44A, 48A, 49A, 50A and 52A all connect from their respective compartments as described before. The injection passageway 21A and aperture 22A for compartment 26A is moved to the opposite edge of cuvette 10A, because of compartment 61. The function of compartment 61 and passageway 62 is to flood *all* passageways of all the compartments with the wash water in compartment 61, when the roller flattens that compartment. Thereafter, when each successive compartment is flattened by the roller, there will be no opportunity for, say, the amplified DNA of compartment 26A to push into any of passageways 48A, 49A, 50A or 52A, because of the water already there. Such water will not adversely affect the transmission of each compartment's contents to the detection compartment.

Compartment 61 can provide an additional advantage of allowing re-constitution of dried reagents stored in compartments 32, 36 and 38. That is, if the light heat seal used as hereinafter described to close off the exit of each compartment to its respective passageway is omitted, and these reagents are dried in their compartments, then when compartment 61 is pressurized by the roller to flood the cuvette, the water of compartment 61 will reconstitute the dried reagents. Optionally, this can be aided by shaking the cuvette. The reconstitution step can occur before or after sample injection into the reaction compartment or amplification within the reaction compartment.

The aforedescribed embodiments feature sequential pressurization of each of the compartments. In addition, simultaneous pressurization of all the liquid containing compartments can be used, provided that pinch points $P_1$-$P_5$ are also used. That is, if pressure is applied to all of $P_1$-$P_5$ to close off the exit passageways except for passageway 44, pressure can be simultaneously applied (by, e.g., appropriately placed air pistons) to all of compartments 26, 30, 32, 34, 36 and 38. However, since only passageway 44 is unblocked, only the amplified DNA will transfer. Thereafter, pinch point P1 only, is released, allowing transfer of wash liquid out through passageway 49, and so forth until pinch point $P_5$ is finally released. Care should be taken to insure the exerted pressure is less than the pressure required to burst the seams confining the liquid in the respective compartments and passageways.

Detection compartment 40, FIGS. 1 and 3, is a flow-by compartment comprising a detecting member 39 that is a supporting sheet 41 on which are disposed piles 43, 43', 43", and 43"'. If the oligo capture method is being used, then each pile comprises polymer beads to which are immovably attached the detection probes noted above, constructed to hybridize with the DNA to be detected. Most preferably, each bead has a different detection probe for a different DNA, so that if enough different piles of beads are present, for example, 8 to 10, tissue typing can be done on the basis of which beads turn color from the dye of compartment 36. Such latex beads are conventional.

Sheet 41 is selected from a material that will bond to the pile of beads, to keep them in place when they are deposited and dried during manufacturing. Various means can be used to secure the beads in place, such as adhesive, or the melting of sheet 41 (if a plastic) to the beads. Useful adhesives include poly(methyl acrylate-co-2-acrylamido-2-methylpropanesulfonic acid, sodium salt-co-2-acetoacetoxyethyl methacrylate) (90:4:6 weight ratios), as described and claimed in commonly owned U.S. Ser. No. 07/837,772, filed on Feb. 18, 1992, by Sutton et al, entitled "ELEMENT AND METHOD FOR NUCLEIC ACID AMPLIFICATION AND DETECTION USING ADHERED PROBES" docket 59622. Useful examples of sheet 41 include nitrocellulose, porous nylon membranes such as those manufactured by Pall Corp., and most preferably a paper coated with latex, or a polyethylene sheet or laminate as described in commonly owned U.S. application Ser. No. 583,106, filed on Sep. 17, 1990, entitled "BEADS FUSED TO A TEST DEVICE SUPPORT". An example of such a latex coated paper is as follows: a paper weighing about 54 g/m² and having a thickness of about 0.6 mm, with a neutral internal sizing, made from about 80% hardwood, can be surface sized and then coated with a latex coating at an average of about 7 g/m², the coating having as its composition conventional industrial grade latex, NaOH at 20 weight %, TSPP as a dispersing agent, opacifying agents such as silicon dioxide and titanium dioxide, hydrasperse clay, and the rest distilled water.

Alternatively, compartment 40 can be completely filled with beads (not shown), so that the amplified nucleic acid material and other solutions flow through the packing of beads. In such a case, the different detection probes for the separate piles 43, 43', 43" and 43''' of FIG. 3 can be "stacked" in a similar fashion, spaced part by beads having no detection probes.

The sheets 12 and 14 are prepared and assembled as follows: sheet 14 is premolded with the compartment indentations formed as shown, FIGS. 1 and 2. With sheet 14 turned upside down, with the indentations forming cups, reagents can be then applied, such as dried reagents 28 and the liquids that go into compartments 30, 32, 34, 36 and 38. Next, sheet 12, now an "upper" sheet, is brought into superposition while essentially flat, except for the mating depression shown at 26', FIG. 2. The two sheets are then lightly anchored together around the perimeter of each compartment as shown by hatching lines, FIG. 1, except at the junction 25 of passageway 21 with compartment 26. For example, a light heat-sealing will bond the two plastic sheets together at these portions, including the outlet of each compartment to its respective exit passageway. This creates a temporary block to liquid proceeding out of a compartment when introduced, a block, however, that is overcome when roller 60 is applied. (Such temporary blocks appear as a broken line at the cross-section of passageways 48, 49, 52 and 54, FIG. 2, and represent a site of separation when liquid is forced out of the compartments leading to this temporary seal).

Thereafter, a heavy seal, e.g., a heat seal, is applied around the circumference of each compartment and its exit passageway, but not across the junction of the passageway to the compartment. It is also applied to the outer periphery 16. The sealing around compartments ensures that liquid pressed out of the compartments will flow only along the respective passageways and not elsewhere between sheets 12 and 14.

When cuvette 10 is used, the patient sample S is injected into compartment 26, FIG. 5, via a pipette 24, at aperture 22. This causes depressed portion 26' to "pop out" enough to become about flush with the rest of sheet 12, shown in phantom in FIG. 2 and in solid line, FIG. 5.

Figure 19:
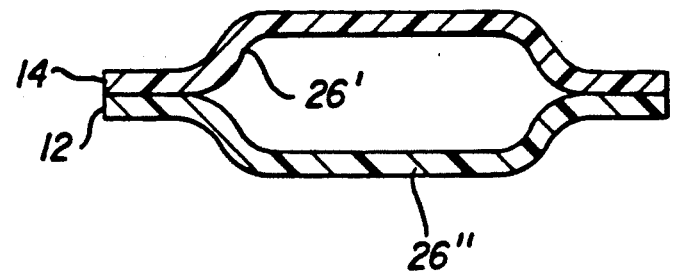
FIG. 19 is a section view similar to that of FIG. 5, but illustrating an alternate embodiment.

Alternatively, portion 26' can be forced to "pop out" beyond the plane of the rest of sheet 12, to form an opposite blister 26", FIG. 19. Furthermore, as shown in FIG. 19, sheets 12 and 14 need not have any metallic component or layer, and can consist entirely of plastic. That is, even just a plastic sheet can provide sufficient rates of thermal transfer.

Figure 4:
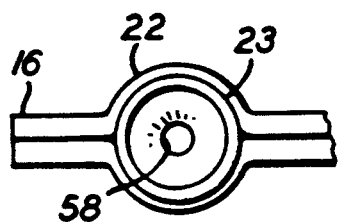
FIG. 4 is a fragmentary section view taken along the line of IV—IV of FIG. 1, but without the pipette.

It is essential that aperture 22, FIGS. 1 and 4, be closable after pipette 24 is withdrawn, prior to the amplification step. This can be accomplished by heat-sealing the aperture closed, or by stoppering the aperture in a suitable fashion, such as by heat-sealing strips 12 and 14 with the heavy seal, or constructing rim 23 with a one-way valve, not shown. If aperture 22 is to be heat-sealed, preferably rim 23 is omitted and pipette 24 is simply pushed directly into the aperture. Whatever mode of closure is used, it should be effective to resist any pressure build-up during PCR amplification or during liquid transfer. Heat-sealing is the preferred method.

As noted above, heating and cooling to provide the needed thermal cycling preferably occurs by heating one or both strips 12 and 14 at compartment 26.

When the amplified DNA enters compartment 40, it is retained there briefly while heat is applied through strip 14, to bring about hybridization. Preferably, strip 14 is transparent at compartment 40 to allow transmission of radiation of suitable wavelength, e.g., visible wavelengths to allow examination of the contents. Compartment 42 can expand to accommodate the liquid influx as well as air influx, since it is preferably deflated prior to use. Alternatively, the instruments used to process the cuvette can include a vacuum plate that pulls compartment 42 out to its inflated shape as shown, FIG. 3, when the waste volume is needed.

Figure 8:
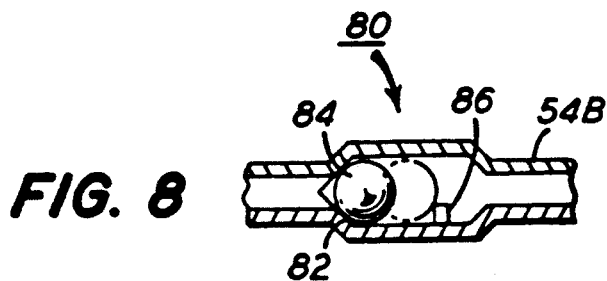
FIG. 8 is a section view taken along the line VIII—VIII of FIG. 7.
Figure 7:
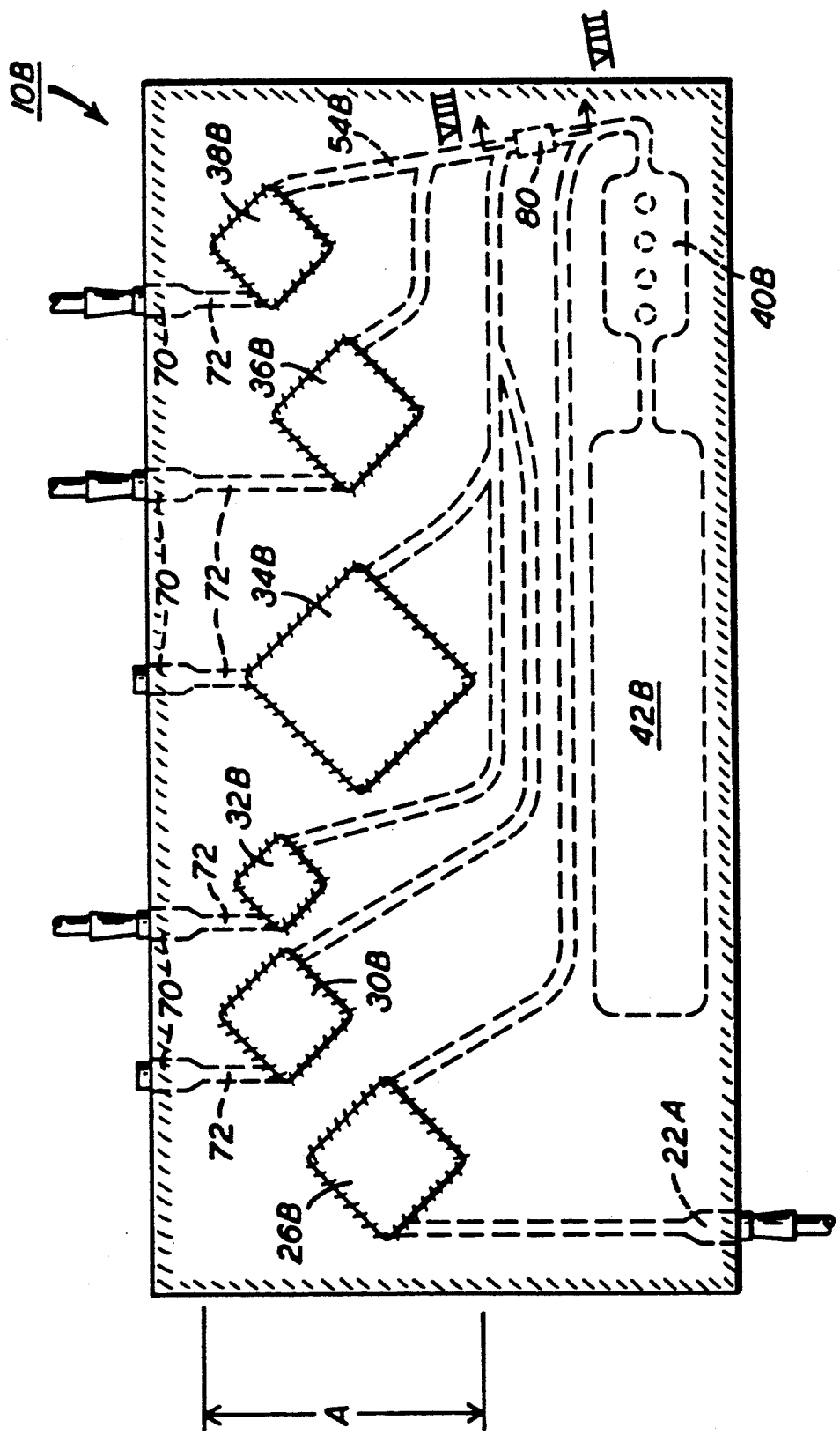
FIG. 7 is a plan view similar to that of FIG. 1, but illustrating an alternate embodiment.

It is not essential that *all* compartments 30-38 be sealed off from the atmosphere during and after amplification, FIGS. 7 and 8, provided they are constructed to prevent a backwash of amplified DNA from entering them. Parts similar to those previously described bear the same reference numeral, to which the distinguishing suffix B has been appended.

Thus, cuvette 10B has all the compartments 26B, 30B, 32B, 34B, 36B, 38B, 40B, and 42B as before, with their passageways interconnecting them so as to function as before. However, each and every one has a liquid injection aperture 70 at the periphery 16B providing, with connecting passageway 72, a fluid path from the atmosphere to the respective compartment. In such a construction, only compartment 26B has liquid in it at the time of DNA amplification, namely sample DNA and the amplifying reagents. (Its injection aperture 22B is closed at this time.) The other compartments can be left open, because of the temporary heat seals formed at their junction with their exit passageways. As an additional safeguard, a check valve 80 can be inserted into passageway 54B to prevent a backwash of DNA into those compartments. Such a valve is conventional, and can comprise, for example, FIG. 8, a seat 82, and a ball 84 which, when pushed back upstream, seats on seat 82 to stop flow. Ball 84 is free, however, to flow downstream up against a small stop 86.

Valve 80 is preferably located in trunk passageway 54B, since this allows one valve to serve all the storage compartments, and it is out of the way of path A, that is, it does not represent an obstacle to the passage of the pressure roller.

After each storage compartment receives its appropriate liquid from a pipette, FIG. 6, and before the pressure roller moves down path A, each aperture 70 is closed tightly in a manner similar to the closure of aperture 22A. Alternatively, apertures 70 can be used as a fill technique to pre-incorporate all the reagents.

In the remaining embodiments, the means for moving the liquids containing, for example, amplified DNA and the detection material, or for fluidly interconnecting all the compartments, instead of a collapsible flexible wall of the compartments, is a piston in a piston chamber that forms the appropriate compartment. That is, the pistons are the equivalent of the flexible walls of the compartments.

Figure 9:
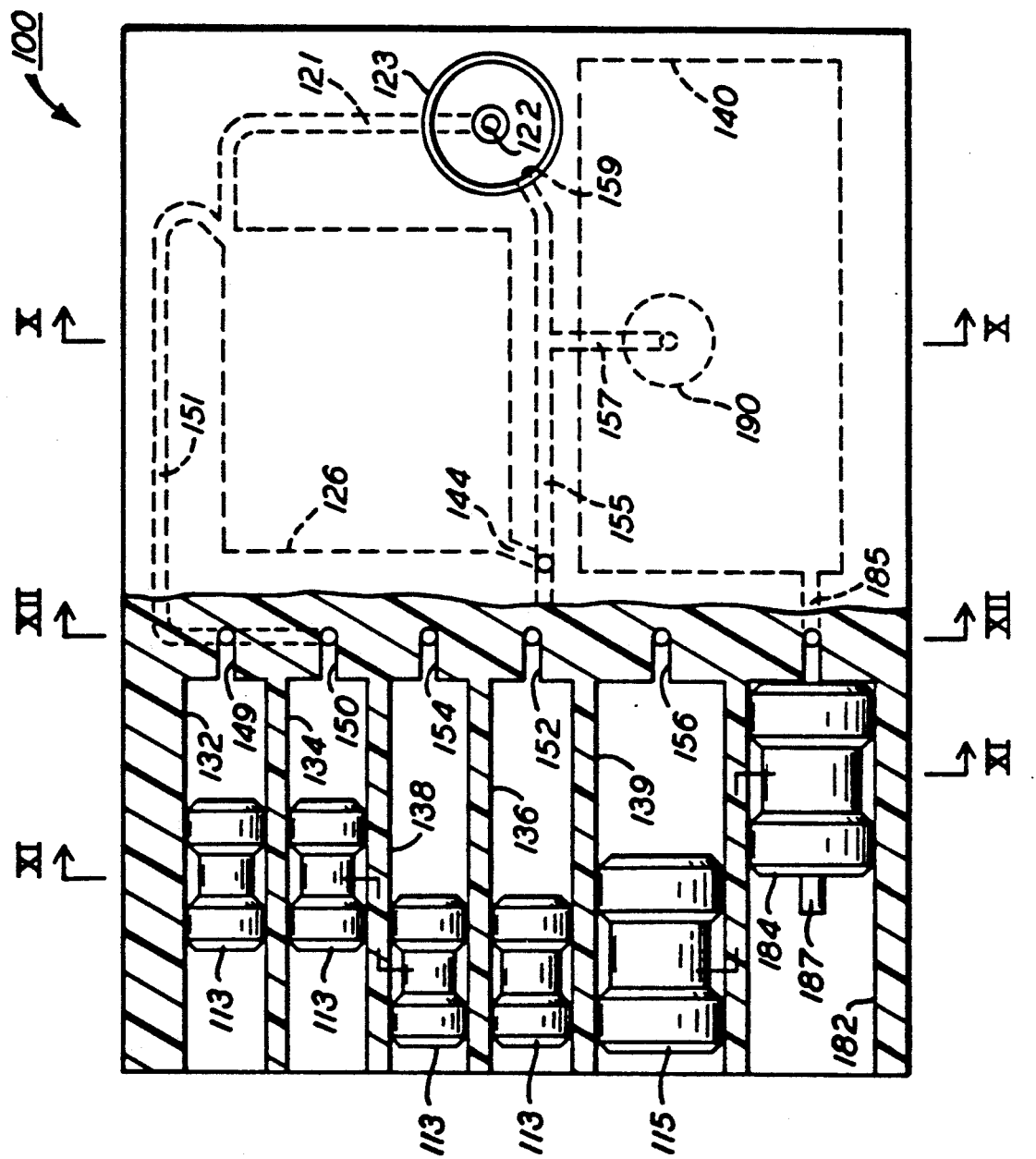
FIG. 9 is a partially sectioned plan view similar to that of FIG. 1, but illustrating an alternate embodiment, the section plane being generally taken along the line IX—IX of FIG. 11.
Figure 10:
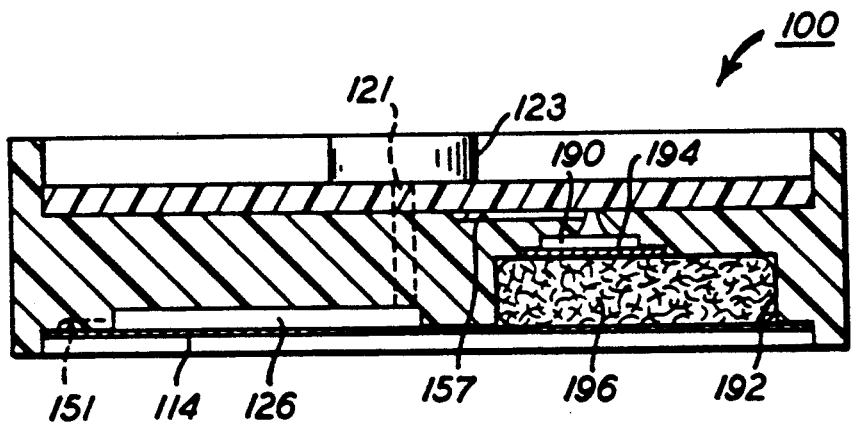
FIGS. 10, 11, and 12 are section views taken generally along the lines X—X, XI—XI, XII—XII, respectively, of FIG. 9.

Thus, in FIGS. 9-12, a cuvette 100, FIG. 9, comprises a reaction compartment 126 having a thermal transfer wall 114, FIG. 10, a detection material storage compartment 132, FIG. 9, a wash storage compartment 134, a leuco dye storage compartment 136, a stop solution storage compartment 138 and another wash storage compartment 139, with respective passageways 144, 149, 150, 152, 154 and 156 leading from each of these. Wall 114 is preferably constructed as for the previous embodiments. Each of these compartments functions as a piston chamber, and mounted within each chamber is a respective piston 113 or 115, disposed outside of the reagent in the compartment. Preferably, the pistons are double-sealing as shown, and include means such as a slot (not shown) for positively engaging a driver actuator for that compartment (not shown). However, passageways 149 and 150 connect with compartment 126, FIGS. 9 and 12, by joining together to form passageway 151. Incoming DNA sample is also fed to compartment 126 via passageway 121 from liquid ingress aperture 122 provided with an exterior shoulder 123, FIG. 9.

Figure 12:
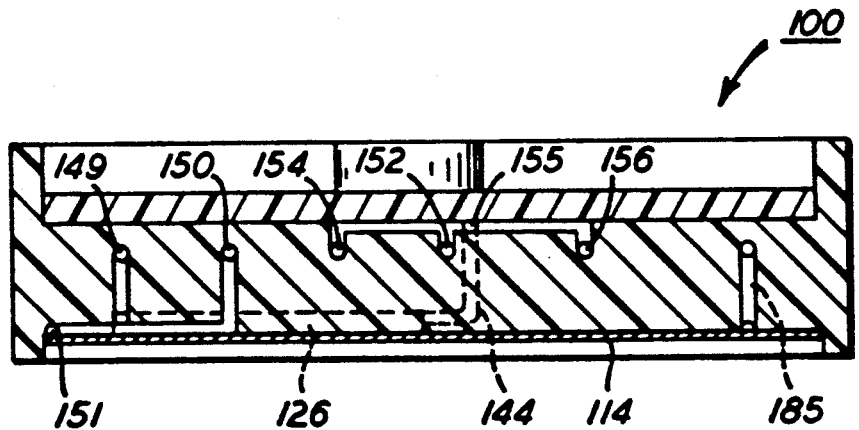

Passageways 152, 154 and 156 join together, FIG. 12, at passageway 155 into which passageway 144 feeds from compartment 126, FIG. 9. Passageway 155 then branches to form passageway 157 leading to compartment 140, and a vent passageway that exits at 159 within shoulder 123. Shoulder 123 is internally threaded, not shown, to receive a stopper that is externally threaded, so that both the ingress aperture 122 and vent aperture 159 can be sealed off by the stopper.

Figure 11:
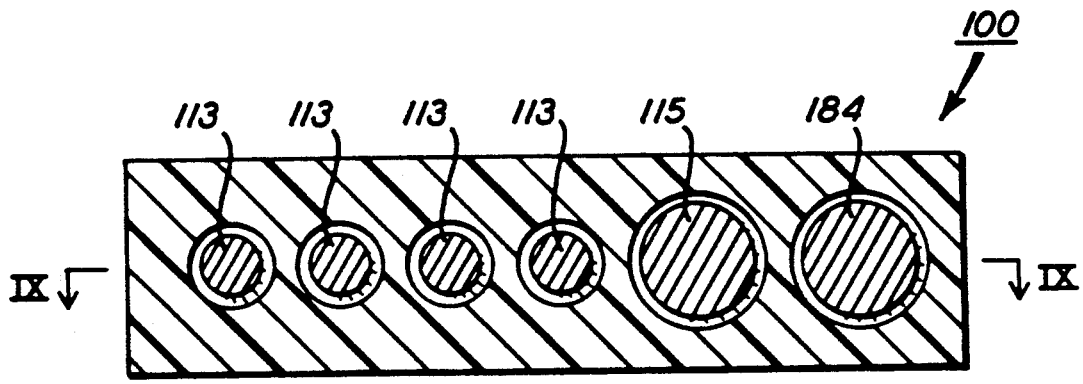

Since there is no flexible wall for expansion, a separate piston chamber 182 and piston 184 is provided to allow air expansion from detection compartment 140, FIGS. 9, 11 and 12. Chamber 182 is connected via passageway 185 to the bottom of compartment 140. This can be done by manually withdrawing piston 184 within its chamber. A stem 187 can project from piston 184 for ease in pulling out that piston.

Referring particularly to FIG. 9, flow-through compartment 140 has an upper portion 190, into which liquid first enters as it is transferred from other compartments, and a lower portion 192, FIG. 10, separated from the upper portion by a permeable membrane 194. Lower portion 192 is substantially filled by an absorbent 196, intended to absorb all the excess liquid that enters compartment 140. Membrane 194 is preferably a cast, woven or electrooptically machined, microfiltration membrane. Any suitable material can be used for absorbent 196, for example, cellulose acetate.

Membrane 194 functions to aid in separation of free, unreacted detection label, from those hybridized to the DNA. That is, the detection probes in compartment 132 are designed both to hydridize onto amplified DNA in compartment 126, and to attach to membrane 194 (or to beads that are trapped by the membrane) once the liquid reaches compartment 140. Such probes also include a label such as horseradish peroxidase, that react with the leuco dye and peroxide when those materials reach compartment 140.

Filling of compartments 132, 134, 136 and 138 can be achieved by adding liquid and then inserting the pistons. Alternatively, prepackaged ampules (not shown) can be inserted, followed by the pistons, the ampules being frangible so that as pressure is applied by the piston, the ampule breaks open to release the liquid.

Transfer of liquid in cuvette 100 is all controlled by the pistons 113, 115, and 184, piston 184 being used to create the vacuum that allows the other pistons to advance.

Alternatively (not shown), an additional compartment and associated piston can be included to feed additional enzyme into compartment 126, so that any deactivation of enzyme by the denaturing step can be countered by the addition of more enzyme.

Thus, the use of cuvette 100 is as follows: starting with the pistons positioned as shown, FIG. 9, sample DNA is introduced via a pipette at aperture 122. Passing through passageway 121, the sample enters compartment 126 where there is already present, or there is co-introduced with the DNA, amplification reagents. The vent aperture 159 and passageway 155 allow the air in compartment 126 to be pushed out by the advancing liquid. Thereafter, a stopper is inserted into shoulder 123, sealing off apertures 122 and 159. Thermal cycling is done on compartment 126, using thermal transfer wall 114, until the desired DNA amplification is achieved. Up until this point, the pistons have not been moved.

Next, piston 113 of compartment 132 is advanced to push the detection material of compartment 132 into compartment 126. That is, in the case of the avidin-bead capture method, the contents of compartment 126 preferably include polymer beads to which is bound via avidin, a biotinylated primer capable of extending with the amplified DNA in an annealing step, to copy the amplified DNA. The compartment also includes a detection probe that is a nucleotide constructed to hybridize with the extended primer attached to a moiety such as horseradish peroxidase. Some wash solution from compartment 134 can be pushed in by piston 115 to insure all of the detection reagents are present in compartment 126, if desired. Mixing can then be achieved by agitating the entire cuvette, by any conventional means. The detection probes are then hydridized to the amplified DNA in compartment 126 by applying thermal control in conventional steps, through wall 114, for example, by heating at 42° C. for five minutes.

Next, additional wash solution is pushed in from compartment 134, to wash the hybridized liquid from compartment 126 to detection compartment 140. Piston 115 is also advanced to push wash from compartment 139 through passageway 156 and 155 to wash any hybridized liquid still remaining in passageway 155, into compartments 140, thus isolating any remaining hybridized liquid in passageway 144 from the leuco dye that is to follow. Enough wash solution is passed through compartments 126 and 140 to insure that all material, such as free detection probes not bound to the trapping means, passes through membrane 194 and into absorbent 196. It is for this wash step, primarily, that piston 184 needs to be withdrawn to prevent back pressure from resisting the transfer of liquid from compartment 126 to compartment 140.

Next, first the leuco dye of compartment 136 and then the stop solution of compartment 138 are advanced into passageways 155 and 157 and then into compartment 140, by advancing their respective pistons 113. This will cause appropriate dye formation at membrane 194 if the amplified DNA is present. (If it is not present, since all free detection material has already washed through into absorbent 196, no color will form and the test will indicate "negative".)

It is not essential that a separate detection compartment be present in order to have a detection site. As is explained regarding the next embodiment, the detection site can be the reaction compartment. Parts similar to these previously described bear the same reference numeral, to which the distinguishing suffix "C" is appended.

Figure 13:
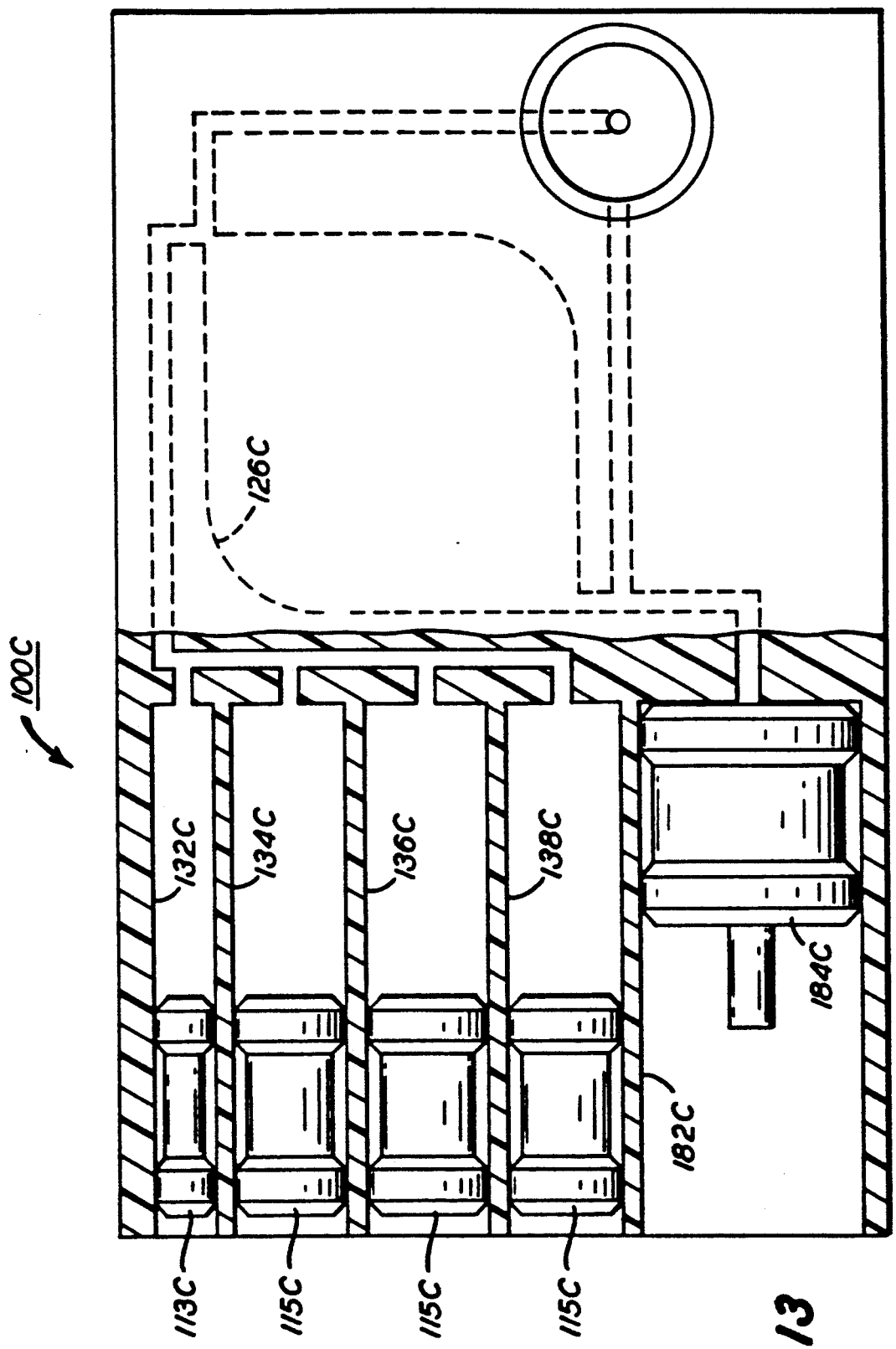
FIG. 13 is a partially sectioned plan view similar to that of FIG. 9, but illustrating yet another embodiment.

Thus, FIG. 13, cuvette 100C has compartments 126C, 132C, 134C, 136C, 138C and their passageways leading to and from each other and from ingress aperture 122C as before. Pistons 113C, 115C and 184C are used to transfer liquid as before, after the DNA amplification that proceeds as before. However, compartment 132C includes as detection reagents, magnetic beads formed from polymers containing magnetic fillers, to which have been bonded the hydridizing material with matching DNA sequences. This is intended to hybridize to one end, for example, of the amplified DNA. The other end of that amplified DNA is intended to hybridize to a detection probe bearing the horseradish peroxidase, as described above.

In this embodiment, separation of the free detection probes not yet hybridized to DNA, from those that are, is achieved as follows: when wash solution is injected from compartment 134C, a magnetic field is supplied below compartment 126C, to retain the bead reagents *and* any detection probe hybridized to an amplified DNA. This causes free detection probes and their labels to be washed out of compartment 126C and into chamber 182C, in which piston 184C has been withdrawn to make room. The magnetic field is further maintained while the leuco dye and the stop liquids are transferred in, causing color to form in compartment 126C, the reaction compartment, if any amplified DNA is present.

Yet other alternatives to the cuvette of FIGS. 8-12 is to extend the compartments 132, 134, 136, 138, 182, or their "C" counterparts, so that they project 90° out of the plane of FIG. 8 (not shown) giving an L-shape to the cuvette. Such an arrangement has the advantages of simplifying mold design and fabrication.

Figure 14:
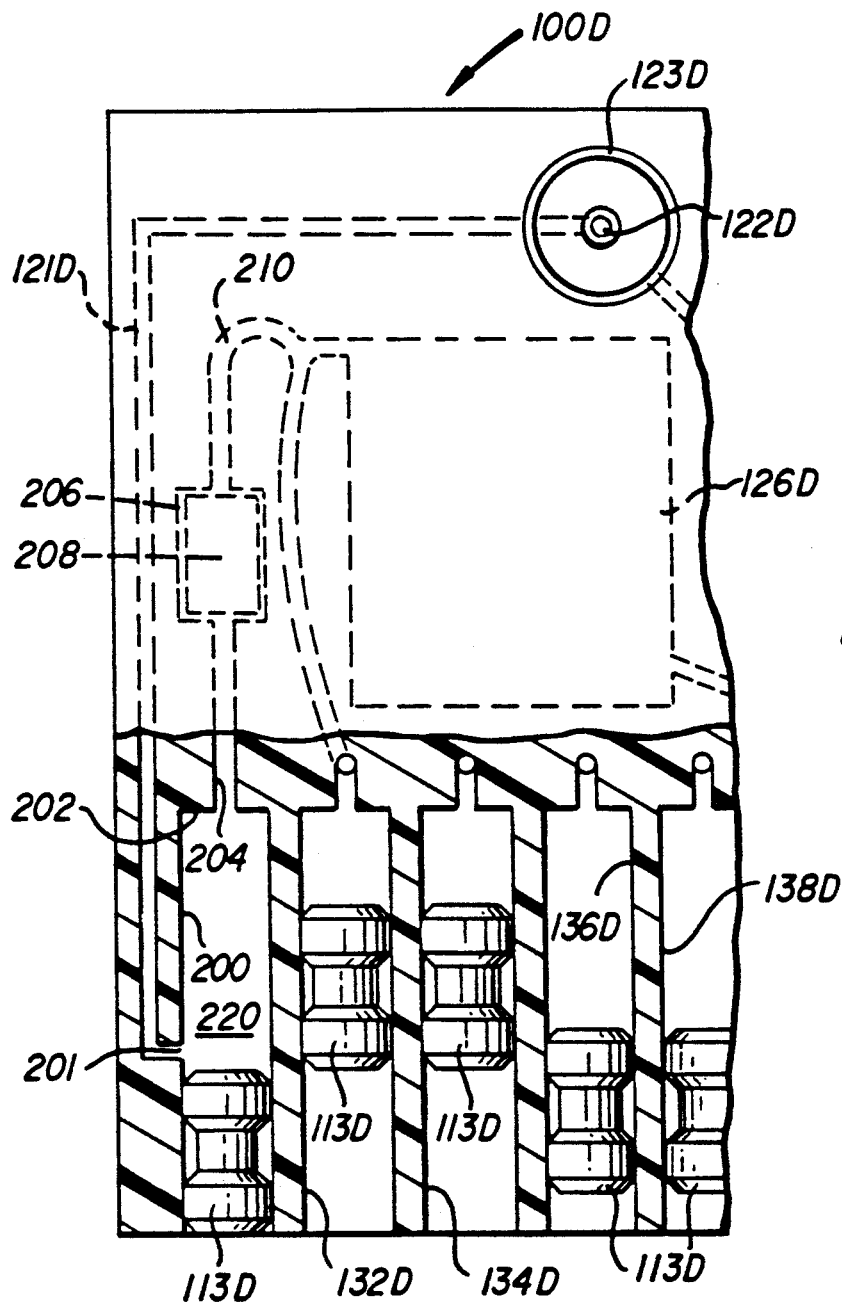

It is possible to extract DNA from cells within the cuvette of the invention, instead of at a stage prior to the use of the cuvette. In such a case, the cuvette is preferably constructed as shown in FIG. 14, wherein parts similar to those previously described bear the same reference numeral, to which the distinguishing suffix "D" is applied.

Thus, cuvette 100D has the same compartments 126D, 132D, 134D, 136D and 138D as before, with pistons 113D being used in the storage compartments. Shoulder 123D protects liquid ingress aperture 122D, and detection is done at a membrane (not shown), all as discussed before. However, passageway 121D, instead of delivering the pipetted liquid sample direct to compartment 126D, the reaction compartment, delivers it to extraction compartment 200. The liquid sample in this case is whole blood or a solution of blood cells, from which the DNA is to be extracted. At the time this liquid sample is added to the cuvette, extracting agents discussed below can be optionally added. Alternatively, they can be preincorporated into compartment 200.

A piston 113D is used in compartment 200, as with the other similar compartments, except that it is fully withdrawn, as shown, to provide maximum room for the introduced sample. Passageway 121D enters compartment 200 at a point 201 just below piston 113D.

At the opposite end 202 of compartment 200, a passageway 204 fluidly connects to an intermediate compartment 206, in which is disposed a filter 208 which the liquid must traverse, in order to reach compartment 126D. Filter 208 has pore sizes adequate to retain cellular fragments in the filter and to pass extracted DNA. For example, a filter made of nylon or polypropylene with pore sizes of about 0.45 microns is particularly useful.

From compartment 206, a passageway 210 carries extracted DNA and solvent (e.g., water) into compartment 126D.

In use, the liquid sample is injected into compartment 200, preferably along with extraction agents, if any. Any DNA extraction protocol can be used, along with concommitant extraction agents, such as surfactants. Highly preferred is a simple heating of the solution to a temperature of about 95° C. for about 5 minutes. Such heating is effective to denature the proteins and lyse the cells. As aids in this extraction method, dextran can be optionally added as a 3 wt % solution, along with a 10 wt % solution of TX-100, which is a non-ionic surfactant available from Rohm and Haas. The heating of compartment 200 can be more rapidly achieved by constructing at least a portion 220 of the wall of the compartment from aluminum, which aluminum extends to the bottom exterior of the cuvette (not shown as a separate surface). The application of heat to the bottom surface of the cuvette adjacent compartment 200 is thus effective to heat compartment 200.

After a suitable incubation period, the contents of compartment 200 are pushed to filter 208 by advancing piston 113D.

Figure 16:
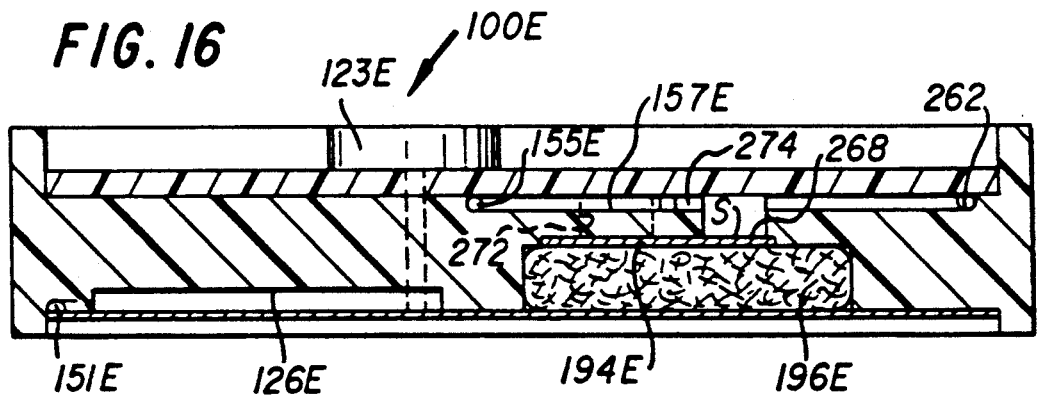
FIG. 16 is a section view taken generally along the line XVI—XVI of FIG. 15.

In some instances, it may be desirable to have a positive and a negative control in the detection compartment, along with the detection site for the DNA of choice. FIGS. 15 and 16 are illustrative of a modification that provides this. Parts similar to those previously described bear the same reference numeral, to which the distinguishing suffix "E" is applied.

Thus, FIG. 15, a cuvette 100E has compartments 126E, 136E, 138E and 182E as before, with appropriate pistons 184E, etc. A passageway 121E carries liquid sample from aperture 122E to reaction compartment 126E, and passageway 151E also feeds liquid to that compartment. Biotinylated primers are delivered from a suitable location, and leuco dye and stop solution are delivered via passageway 155E to passageway 157E that is directed to the detection site. Passageway 144E provides access of the DNA product produced in compartment 126E, to those passageways 155E and 157E. Liquid coming from passageway 157E encounters a detection membrane 194E disposed in contact with absorbent 196E, FIG. 16, all as in the previous embodiments.

However, unlike previous embodiments, there are separate regions at membrane 194E for the sample DNA detection, labeled "S"; for a positive control, labeled "+"; and for a negative control, labeled "−", FIG. 15. The purpose of the positive control is to ensure that the reagents *will* produce a signal for DNA (preferably a color), if the DNA is present—that is, to alert the user if the reagents are defective in any way by *failing* to produce a signal at the "+" region. The negative control on the other hand should not produce a signal. The primary purpose of the negative control is to give the user a background color against which the sample color is to be compared. That is, a faint background color may occur in the reagents for extraneous reasons, and it is important that the sample color be significantly greater in density than this, before a "positive" read is attributed to the test.

There are several ways in which this can be done. In the embodiment of FIGS. 15 and 16, the method used is the avidin-bead capture. This method features the use of avidin or streptavidin covalently attached to beads, biotinylated primers, and labeled detection probes as part of the detection material. Preferably at least the probes are kept in storage compartments 250, 252 and 254, FIG. 15. Each compartment is dedicated to a single type of detection probe—compartment 250 has the sample DNA probes, 252 the negative control probes, and 254 the positive control probes. Pistons 260 are used to pressurize their respective compartments, preferably simultaneously, to force the contents out through respective passageways 262, 264 and 266 into the detection compartment 268, 270 and 272 associated with each probe and each probe passageway. Thus, each detection compartment has only its probe therein, and none of the other two.

To feed amplified DNA and other reagents to all three detection compartments, passageway 157E preferably splits into three branches 274, 276, and 278, FIGS. 15 and 16, that connect with the detection compartments.

It will be readily appreciated that two of the three probes have a genetic material that is complementary to the appropriate DNA. The probe for the sample has a genetic complement to the targeted DNA of the sample. The positive probe has a genetic complement for a DNA material that is always present, which at least in the case of blood cells, is preferably beta-globin. The negative probe has a genetic complement that matches no known amplified DNA from the sample. This is done most easily by constructing the probe complement with any genetic code that is random in sequence, hence a "nonsense" code.

As will be apparent, the process works as follows: the avidin-bearing beads are preferably stored with the probes in compartments 250, 252 and 254. As amplified DNA is supplied via passageways 274, 276 and 278 to the respective detection compartments, pistons 260 are advanced to push the appropriate probes and beads into those detection compartments. Those compartments are appropriately heated to cause the amplified DNA to hybridize specifically in compartments 268 and 272 to the appropriate probe from compartments 250 and 254. Preferably, no hybridization occurs in detection compartment 270, since there should be no "nonsense" DNA present to react with the negative control probe. Thereafter, wash solution is pushed through the detection compartments to wash through membrane 194E, any labeled probes not hybridized and thus not attached to beads, into the absorbent 196E. The wash is followed by contact with the leuco dye solution, and then contact with the stop solution.

Yet another method that can be used is the so-called oligo capture technique. In this technique, FIGS. 17 and 18, the labeled probes are stored in immobilized form, already on the detection membrane prior to the introduction of amplified DNA. Parts similar to those previously described bear the same reference numeral, to which the distinguishing suffix "F" is appended.

The oligo capture method used in this embodiment features probes immobilized either on the membrane, or on the above-mentioned beads that are trapped on or in the membrane, such probes containing genetic material that is complementary to the appropriate DNA. In another compartment (139F), labeled avidin for reaction with biotin on the amplified DNA is stored for which the label can be, for example, horseradish peroxidase.

Figure 17:
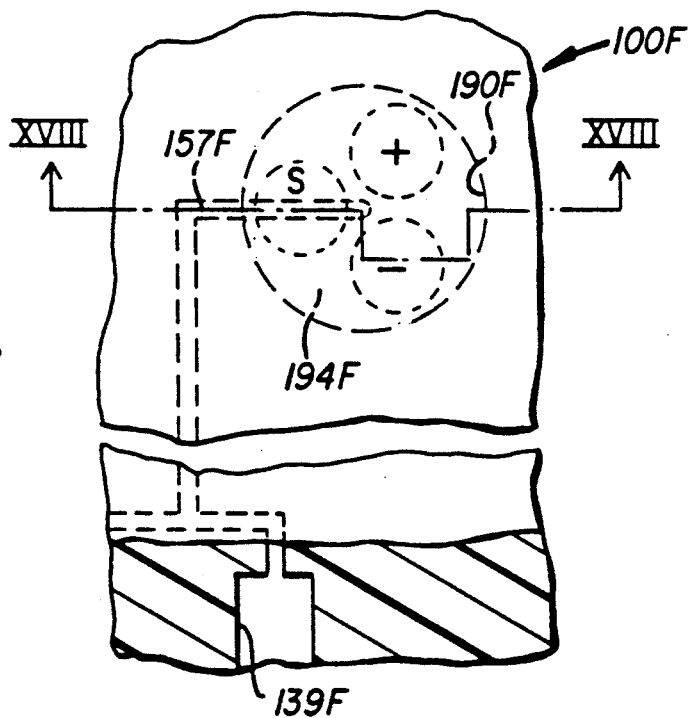
FIG. 17 is a fragmentary plan view partially in section, similar to FIG. 9 and illustrating still another embodiment.
Figure 18:
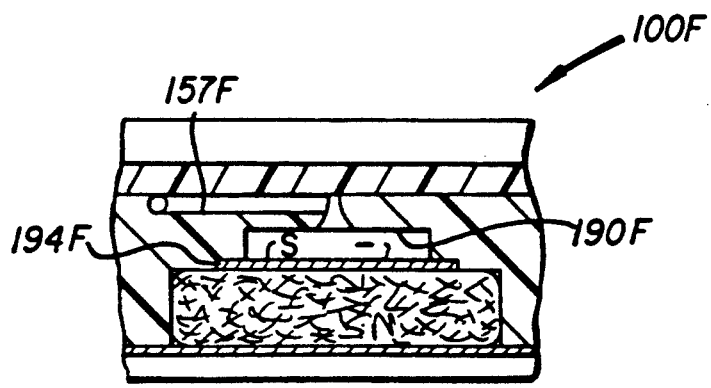
FIG. 18 is a section view taken generally along the line XVIII—XVIII of FIG. 17.

Thus, FIGS. 17 and 18, cuvette 100F is identical to that of the embodiment of FIG. 9, except as to the detection compartment 190F and what is stored in storage-compartment 139F, FIG. 17. More specifically, the sample DNA probe is immobilized on portion "S" of membrane 194F, the positive control probe is immobilized on portion "+", and the negative control probe is immobilized on portion "−". Each portion of membrane 194F bearing such probes is preferably not in contact with the other portions.

The procedure in this case is to force amplified DNA via passageway 157F into detection compartment 190F, to flow over the entire surface of membrane 194F. Appropriate heating causes amplified target DNA to hybridize specifically and thus attach to the probe in the "S" area, the ubiquitous DNA to attach to the probe in the "+" area, and preferably nothing to hybridize at the "−" area. A wash solution is forced into compartment 190F, e.g. from 134F or elsewhere, followed by avidin-label, which then reacts with the biotinylated product now hybridized to either the amplified target DNA or the positive control DNA. Thereafter, a wash solution is added, and then leuco dye and stop solution are added.

The cuvettes described above are also useful in amplifying DNA by other techniques. For example, LCR is a procedure known to be generally equivalent to PCR, wherein "LCR" stands for "ligase chain reaction". Thus, the procedure for LCR parallels that described immediately after "PCR Technology" above, as follows:

LCR TECHNOLOGY

The process is identical to the PCR steps, in its detailed protocol, except as follows:

In step 3) at least two probes, rather than primers, anneal to the template strands, in a fashion such that the 3' end of one probe is immediately adjacent to the 5' end of the adjacent probe annealed to the same template strand. "Probe" as is used for LCR means, an oligonucleotide capable of being LIGATED to an adjacent probe. At least one of these probes is preferably biotinylated. The temperature of this step is selected to be between 30° C. and about 75° C.

In step 4), necessarily the heating step is used with a *ligase* enzyme, rather than a polymerase enzyme, to ligate or join the two adjacent probes together, as is well-known. Preferably, the ligase is a thermostable enzyme. Again, the temperature of this step should be between 30° C. and about 75° C.

Expressed in terms of the cuvette shown in FIG. 1, the only modifications required to do amplification by LCR instead of PCR, are as follows: Compartment 26 contains ligase and one or both of the probes noted above. The detection material in compartment 32 can be avidin bound to the horseradish peroxidase. The remaining compartments are as described for PCR amplification, except that the piles of beads in compartment 40 have bound thereto, a probe that will anneal across the junction of the two ligated probes. Thus this last probe contains bases that are complimentary to a few (e.g., 15) bases on each side of the ligated junction. This probe anneals by maintaining, during detection, the temperature above the temperature $T_1$ at which the probe will hybridize to either of the 2 ligating probes, and at or below the higher hybridizing temperature $T_2$ of that probe to the longer ligated product. It is well known that $T_2$ usually is substantially higher than $T_1$, unless offset by a higher "GC" content of the shorter probe (which is to be avoided.) This insures that the probe on the bead hybridizes to the ligated LCR product, but any "free", unligated probes that happen to be present do *not* anneal or hybridize to the ligated product. Such unligated probes then wash out of compartment 40.

Dye development at compartment 40 can be allowed to proceed for a time of from about 30 seconds to about 15 minutes, prior to the addition of the stop solution.

Alternatively, the stop solution can be omitted in those instances in which a changing dye density is not a problem, e.g., if the detection chamber will be read at a predetermined time in each case.

Further details of LCR processing can be found in, e.g., *Science*, Vol. 241, p. 1077-1080, Aug. 26, 1988.

The invention has been described in detail with particular reference to preferred embodiments thereof, but it will be understood that variations and modifications can be effected within the spirit and scope of the invention.

What is claimed is:

1. A method for amplifying and detecting nucleic acid material in a closed cuvette without allowing aerosols to exit therefrom to contaminate the environment, the method comprising the steps of
   a) providing within a reaction compartment of a cuvette a sample of nucleic acid material and amplifying reagents, said cuvette comprising a plurality of compartments including said reaction compartment and storage means for storing a detection material, at least one of said compartments including a detection site, and means for interconnecting said compartments to provide fluid transfer;
   b) closing off permanently the portions of said cuvette containing the nucleic acid material to lock all nucleic acid into said cuvette;
   c) amplifying the nucleic acid material by cycling said reaction compartment through temperature changes preselected to cause said reagents to be effective to amplify said temperature changes including temperatures exceeding 37° C.;
   d) fluidly transferring amplified nucleic acid material and detection material to said detection site while keeping said cuvette closed against leakage of nucleic acid material outside of the cuvette; and
   e) detecting the amplified nucleic acid material at said detection site with said detection material, all while the nucleic acid material remains confined within said cuvette.

2. A method for amplifying and detecting nucleic acid material in a closed cuvette without allowing aerosols to exit therefrom to contaminate the environment, the method comprising the steps of
   a) placing a sample suspected of containing a target nucleic acid material, and amplifying reagents, into a cuvette comprising a reaction compartment, a detection site, reagents effective to provide detection of the target nucleic acid material, and means allowing transfer of amplified nucleic acid material to said detection site;
   b) closing off permanently the portions of said cuvette containing the nucleic acid material to lock all nucleic acid material into said cuvette;
   c) amplifying the nucleic acid material by cycling said reaction compartment through temperature changes that include temperatures in excess of 37° C. and which are preselected to cause said reagents to be effective;
   d) fluidly transferring amplified nucleic acid material to said detection site;
   e) interacting at said detection site, any amplified target nucleic acid material with detection reagents;
   f) detecting the amplified nucleic acid material at such detection site, and
   g) during steps c) through f), maintaining the cuvette closed to the atmosphere so that all nucleic acid material remains confined within the cuvette and carry-over contamination is prevented.

3. A method as defined in claim 1 or 2, wherein said step c) comprises the step of transferring heat across a wall of said reaction compartment, both into and out of said compartment, said wall comprising at least one thermally conductive material.

4. A method as defined in claim 3, wherein said wall has a thermal path length of no more than about 0.3 mm and a thermal resistance of no more than about 5.0° C./watt.

5. A method as defined in claim 1 or 2, wherein at least one wall of said compartments is sufficiently flexible as to allow external pressure to compress said compartments to force liquid transfer out of said compartments, and wherein said step d) comprises the step of applying exterior pressure to said flexible walls of said compartments in a predetermined sequence.

6. A method as defined in claim 1 or 2, wherein said detection material include a bead comprising a magnetizable material and wherein said steps d)-e) comprise the steps of transferring said beads to said reaction compartment, attaching said detection material, including said beads, to said amplified nucleic acid material and washing away unattached detection material in the presence of a magnetic field that retains said beads and attached detection material within said reaction compartment.

7. A method as defined in claim 1, wherein said steps d) and e) occur sequentially by pressurizing first said reaction compartment and thereafter a storage compartment.

8. A method as defined in claim 1, wherein said steps d) and e) occur by pressurizing said storage compartment and said reaction compartment simultaneously, and retarding the flow of detection material until amplified nucleic acid material has been transferred to said site.

9. A method as defined in claim 1, and further including as a step prior to said step e), the step of reconstituting detection material deposited in dried form in a storage compartment, by transferring pre-incorporated water to said dried material from a storage compartment.

10. A method as defined in claim 1, wherein step a) comprises the step of injecting at least blood cells and optional DNA extraction agents into a predetermined one of said compartments to form a solution;
   and before step c), further including the steps of:
   i) extracting DNA from the cells in said predetermined compartment; and
   ii) after a suitable incubation period, forcing said solution of extracted DNA and cell fragments through a filter disposed between said predetermined one compartment and said reaction compartment, said filter being sized to retain cellular fragments and to pass DNA.

11. A method as defined in claim 1 or 2, wherein said amplifying reagents include a polymerase and said amplifying step includes extending a primer annealed to a DNA strand by the action of said polymerase, to form a double-stranded DNA.

12. A method as defined in claim 11, wherein said extending step is followed by heating at a predetermined temperature to separate the newly formed double-stranded DNA into single strands.

13. A method as defined in claim 1, wherein said cuvette further includes a first piston chamber and a first piston in said chamber, fluidly connected to said reaction compartment so that the advance of said piston in said chamber causes pressure to be increased in said reaction compartment, and a second piston chamber and piston therein, fluidly connected to said detection site so that when said second piston is withdrawn in its chamber, it relieves pressure at said detection site and said step d) comprises the step of advancing said first piston while withdrawing said second piston.

14. A method as defined in claims 1 or 13 wherein said step of detecting is done while heating said detection site in an amount sufficient to hybridize reagents used for said detecting.

15. A method as defined in claim 13, wherein said detection reagents are incorporated into the cuvette prior to said step c).

* * * * *

UNITED STATES PATENT AND TRADEMARK OFFICE
CERTIFICATE OF CORRECTION

PATENT NO. : 5,229,297
DATED : July 20, 1993
INVENTOR(S) : Paul N. Schipelsky, et al It is certified that error appears in the above-indentified patent and that said Letters Patent is hereby corrected as shown below:

Column 21, line 42 reads "effective to amplify said temperature changes in-"

Column 21, line 42 should read --effective to amplify, said temperature changes in--

Signed and Sealed this

First Day of March, 1994

Attest:

BRUCE LEHMAN

*Attesting Officer*  *Commissioner of Patents and Trademarks*